US006868853B1

(12) United States Patent
Nilsson et al.

(10) Patent No.: US 6,868,853 B1
(45) Date of Patent: Mar. 22, 2005

(54) METERED ELECTRO-DOSE

(75) Inventors: Thomas Nilsson, Mariefred (SE); Lars-Gunnar Nilsson, Köping (SE)

(73) Assignee: Microdrug AG, Hergiswil NW (CH)

( * ) Notice: Subject to any disclaimer, the term of this patent is extended or adjusted under 35 U.S.C. 154(b) by 654 days.

(21) Appl. No.: 09/664,385

(22) Filed: Sep. 18, 2000

(30) Foreign Application Priority Data

Aug. 31, 2000 (SE) .............................................. 0003082

(51) Int. Cl.[7] .............................................. A61M 15/00

(52) U.S. Cl. ............................ 128/203.15; 128/203.12; 424/489

(58) Field of Search ....................... 128/203.15, 203.12; 604/58; 424/46, 489; 514/951; 118/621, 624

(56) References Cited

U.S. PATENT DOCUMENTS

| | | | | |
|---|---|---|---|---|
| 5,714,007 A | * | 2/1998 | Pletcher et al. | 118/629 |
| 6,007,630 A | * | 12/1999 | Pletcher et al. | 118/624 |
| 6,063,194 A | * | 5/2000 | Poliniak et al. | 118/623 |
| 6,565,885 B1 | * | 5/2003 | Tarara et al. | 424/489 |
| 6,638,495 B2 | * | 10/2003 | Weers et al. | 424/45 |

FOREIGN PATENT DOCUMENTS

| | | |
|---|---|---|
| WO | 97/00704 | 1/1997 |
| WO | 98/32479 | 7/1998 |
| WO | WO 98/32479 | 7/1998 |
| WO | 00/06235 | 2/2000 |
| WO | 00/06236 | 2/2000 |

* cited by examiner

*Primary Examiner*—Henry Bennett
*Assistant Examiner*—Mital Patel
(74) *Attorney, Agent, or Firm*—Young & Thompson

(57) ABSTRACT

An electro-dose constitutes a metered medical powder and is formed from an electro-powder constituting an active powder substance or a dry powder medical formulation being transferred onto a device member forming a dose carrier. The electro-dose prepared from an electro-powder presents a fine particle fraction (FPF) having of the order 50% or more of its content with a particle size between 0.5–5 $\mu$m. The electro-powder of such a metered electro-dose further provides electrostatic properties regarding absolute specific charge per mass after charging of the order 0.1 to 25 $\mu$C/g and presents a charge decay rate constant $Q_{50}$ of more than 0.1 sec with a tap density of less than 0.8 g/ml and a water activity $a_w$ of less than 0.5. The electro-dose porosity is adjusted to obtain an optimized porosity value in percent of 75 to 99.9 calculated as $100-100\times(\text{Density}_{electro\text{-}dose}/\text{Density}_{electro\text{-}powder})$.

4 Claims, 13 Drawing Sheets

METERED ELECTRO-DOSE

TECHNICAL FIELD

The present invention relates to electrostatic dosing and more particularly to an electro-dose using electro-powder as well as a process and a method for preparation of a metered electro-dose for inhalation into the deep or upper lungs by means of an inhaler device.

BACKGROUND

The dosing of drugs is carried out in a number of different ways in the to medical service today. Within health care more and more is focused on the possibility of dosing medical drugs as a powder directly to the airways and lungs of a patient by means of an inhaler in order to obtain an effective, quick and patient-friendly administration of such substances.

A dry powder inhaler, DPI, represents a device intended for administration of powder into the deep or upper lung airways by oral inhalation. With deep lung should be understood the peripheral lung and alveoli, where direct transport of active substance to the blood can take place. Particle sizes, to reach into the deep lung, should be in a range 0.5–3 $\mu$m and for a local lung a delivery in the range 3–5 $\mu$m. A larger grain size will easily stick in the mouth and throat, and a smaller grain size may accompany the expiration air out again.

To succeed with systemic delivery of medical powders to the deep lung by inhalation there are some criteria, which have to be fulfilled. The most important is a very high degree of de-agglomeration of the medical powder but also an exact dose is of great importance. This is not possible with dry powder inhalers of today without special arrangements as for example a so called spacer.

By means of a spacer the small grains are evenly distributed in a container from which the inhalation can take pace. Upon inhalation from the spacer the fine powder floating free in the air will effectively reach the alveoli of the lung. This method in principle has two drawbacks, firstly difficulties to control the amount of medicine emitted to the lung as an uncontrolled amount of powder sticks to the walls of the spacer and secondly difficulties in handling the relatively space demanding apparatus.

Powders for inhalers have a tendency of agglomerating, in other word to clod or to form small or larger lumps, which then have to be de-agglomerated. De-agglomeration is defined as breaking up agglomerated powder by introducing electrical, mechanical, or aerodynamic energy. Usually de-agglomeration is performed as a stage one during dosing and as a final stage two during the patient's inspiration through the DPI.

Inhaler devices normally use the force exerted by the patient's more or less normal inspiration effort for de-agglomerating the medical substance administered when inhaling in an effort to bring as much as possible of the active substance into the lungs. This often leads to inhaler de signs using high pressure drops, which will put the patient's lungpower to the test.

One major problem with some of the technique described above is to also obtain a low relative standard deviation (RSD) between doses with this type of technique due to lack of in line control possibilities in production mating it hard to be in compliance with regulatory demands.

As already noted for an optimum amount of substance to reach the alveoli, an administered powder dose should preferably have a grain size between 0.5 and 3 $\mu$m. Besides, the inspiration must take place in a calm way to decrease air speed and thereby reduce deposition in the upper respiratory tracts.

Technologies to de-agglomerate today include advanced mechanical and aerodynamic systems and combinations between electrical and mechanical filling systems that can be seen in for instance in U.S. Pat. No. 5,826,633. Further there are systems disclosed for dispersing aerosolized doses of medicaments, e.g. U.S. Pat. Nos. 5,775,320, 5,785,049, and 5,740,794. Furthermore, in our International Publications WO 00/0636 and WO 00/6235 principles for de-agglomeration and classification are disclosed.

The term electro-powder refers to a micronized medical powder presenting controlled electrostatic properties to be suitable for electrostatic administration in an inhaler device. Such an electro-powder provides possibilities for a better dosing from electrostatically operating equipment such as disclosed in our U.S. Pat. No. 6,089,227 as well as our Swedish Patents No. 9802648-7 and 9802649-5, which present excellent inhalation dosing performance.

The state of the art also discloses a number of solutions for depositing powder for dosing. U.S. Pat. No. 6,063,194 discloses a powder deposition apparatus for depositing grains on a substrate using an electrostatic chuck having one or more collection zones and using an optical detection for quantifying the amount of grains deposited. U.S. Pat. Nos. 5,714,007 and 6,007,630 disclose an apparatuses for electrostatically depositing a medicament powder upon predefined regions of a substrate, the substrates being used to fabricate suppositories, inhalants, tablet capsules and the like. In U.S. Pat. Nos. 5,699,649 and 5,960,609 are presented metering and packaging methods and devices for pharmaceuticals and drugs, the methods using electrostatic phototechnology to package microgram quantities of fine powders in discrete capsule and tablet form.

Devices of prior art technology does often not reach a sufficiently high degree of de-agglomeration and an exact dose is not well developed and leaves much to be desired when it comes to dosage conformity and lung deposition effectiveness of the medical substance. Therefore, there is still a demand of pre-fabricated high accuracy pre-metered doses to be loaded into an inhaler device, which then will ensure repeated exact doses to be given. The active dry powder then must possess a fine particle fraction, which guarantees its administration to a position within the lung of a patient where it will exert its expected effect.

SUMMARY

An electro-dose and a method and a process for obtaining an electro-dose are disclosed. The electro-dose constitutes a pre-metered medical powder intended for use in a dry powder inhaler and is formed from an electro-powder constituting an active powder substance or a dry powder medical formulation being onto a device member forming a dose carrier. The electro-dose prepared from an electro-powder presenting a fine particle fraction (FPF) having of the order 50% or more of its content with a particle size between 0.5–5 $\mu$m. The electro-powder of such a pre-metered electro-dose further provides electrostatic properties regarding absolute specific charge per mass after charging of the order 0.1 to 25 $\mu$C/g and presents a charge decay rate constant $Q_{50}$ of more than 0.1 sec with a tap density of less than 0.8 g/ml and a water activity $a_w$ of less than 0.5.

The electro-dose porosity is adjusted by means of a mechanical and/or electrical vibration of the dose receiving device member during the electro-dose build-up operation to obtain an optimized porosity value of 75 to 99.9% calculated as $100-100\times(\text{Density}_{electro\text{-}dose}/\text{Density}_{electro\text{-}powder})$. A number of parameters must be kept under strict control during the processing in order to obtain the desired electro-dose for utilization in a dry powder inhaler.

SHORT DESCRIPTION OF THE DRAWINGS

The invention, together with further objects and advantages thereof, may best be understood by making reference to the following description taken together with the accompanying drawings, in which.

DESCRIPTION

Figure 1:
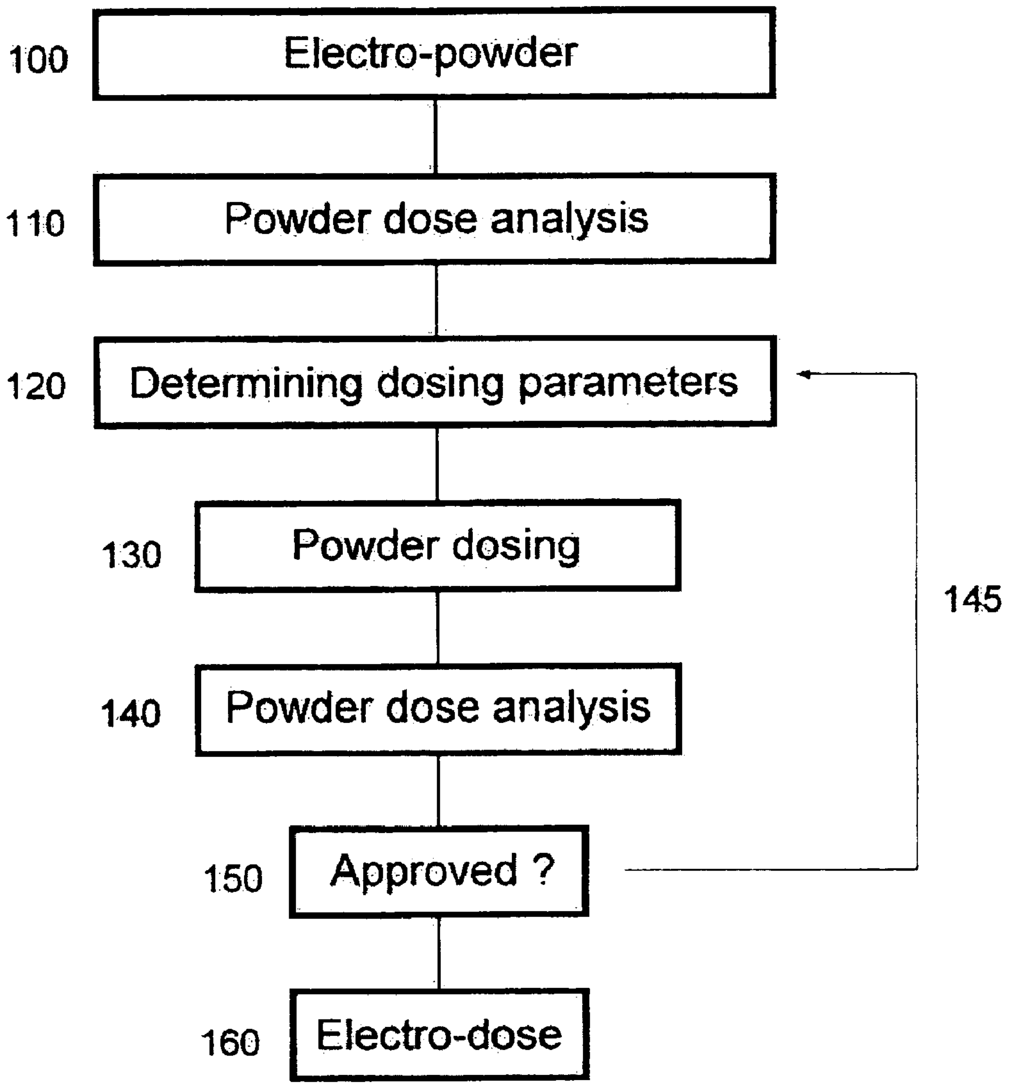
FIG. 1 is a simplified flow chart for creating an electro-dose from an electro-powder.

In a starting step 100 of FIG. 1 an electrostatically dosed electro-powder is brought into a powder dose analysis step 110. Dosing parameters are then determined in a step 120 to finally result in an electro-dose in a step 160. Electro-powder here is defined as a prepared active substance meeting a set of electrical specifications for optimum electrostatic dosing properties. Specific charge is expressed in Coulomb per mass unit in this context as $\mu C/g$ after charging. Such an electro-powder should present an absolute specific charge, after charging by induction, corona, or tribo-charging, of the order of 0.1 to 25 $\mu C/g$ ($0.1\times10-6-25\times10-6$ Coulomb/gram of negative or positive charge) and a discharge rate constant $Q_{50}>0.1$ sec. $Q_{50}$ is defined as the time until 50% of the electrostatic charge is discharged, (for instance after a corona charging in an Electrical Low Pressure Impactor (ELPI) model 3935 from DEKATI LTD). Furthermore the electro-powder should constitute a powder with more than 50% of fine particle fraction with a particle size less than 5 $\mu m$ and have a water content of less than 4% together with a water activity $a_w<0.5$, preferably being between 0.2 and 0.3 and a tap density of less than 0.8 g/ml.

Water content is defined as the amount of weakly bound water. It's calculated as the difference between the total water content, determined eg by Karl-Fischer titration, and the amount of strongly bound water, e.g. crystal water, characteristic for the substance. Water activity $a_w$ is a dimensionless quantity, which may, for instance, be measured with an AquaLab model series 3 TE. Tap density is, for instance, measured by using a Dual Autotap from Quantachrome® Corporation according to British Pharmacopoeia for Apparent Volume method. Both water activity and tap density are quantities well know to a person skilled in the field of chemistry analysis.

All measurements are performed at room temperature defined as in a range of 18–25° C. in air or nitrogen atmosphere with a relative humidity less than 5%. The absolute specific charge is the charge the electro-powder presents after an electrostatic charging being performed and subsequently measured in $\mu C/g$ with an electrometer, e.g. a Keithley Electrometer 6512 or an Electrical Low Pressure Impactor (ELPI) model 3935 from DEKATI LTD.

The electro-dose is then defined as an electrostatically dosed electro-powder possessing the following specification: Porosity defined as $Dp_{electro\text{-}dose}=100-100(\text{density}_{electro\text{-}dose}/\text{density}_{electro\text{-}dose})<75\%$ and having a optimized de-agglomeration of >25% and more preferable being more than 50% and most preferable more than 75% and meeting a dosage uniformity according to USP 24-NF 19 Supplement 601 Aerosols/Physical Tests pages 2674–2688, which will hereafter be referred to as USP, and also possessing a de-agglomeration difference measured according to USP compared with the de-agglomeration at a flow representing a pressure drop over the inhaler device reduced to 1 kPa $(1-(\text{de-agglomeration}(Q_{1\ kPa})/\text{de-agglomeration}(Q))\times100)<25\%$ and more preferably less than 10% and most preferably less than 5%.

Particles intended for the deep lung, here defined as the peripheral lung and alveoli, where direct transport of an active substance to the blood can take place, should have a particle size in the range 0.5–3 $\mu m$. For treatment in the local lung, defined as upper parts of the lung, where treatment normally takes place for instance in asthma treatment, the particle size should be in the range 3–5 $\mu m$. All particle sizes are defined as the size of the particles measured with for instance a laser diffraction instrument e.g. a Malvern Mastersizer for physical size classification or an Andersen Impactor for an aerodynamic size classification and if not stated otherwise always referred to as aerodynamic particle size.

The active substance is a pharmaceutical active chemical or biological substance intended for administration into the deep or upper lung airways by oral inhalation from a dry powder inhaler device (DPI), where inhaled macromolecules could be from the following therapeutic areas: Insulin rapid intermediate and slow acting and diabetes peptides, interferons, interleukins and antagonists, antibodies, peptides for immune suppression, nerve growth factors, vaccines, gene therapies) genetically modified virons and/or bacterias, parathyroid hormone, osteoporosis peptides, anti-obesity peptides, luteinizing hormone releasing hormone (LHRH) and LHRH analogs, somatostatin analogs, human calcitonin, colony stimulating factor, erythropoietins, growth hormones, erectile dysfunction, anti-pregnancy hormones.

The active substance also could be selected from the pharmaceutical active chemical and biological substances vasopressin, a vasopressin analogue, desmopressin, glucagon, corticotropin, gonadotropin, calcitonin, C-peptide of insulin, parathyroid hormone, human growth hormone, growth hormone, growth hormone releasing hormone, oxytocin, corticotropin releasing hormone, a somatostatin analogue, a gonadotropin agonist analogue, atrial natriuretic peptide, thyroxine releasing hormone, follicle stimulating hormone, prolactin, an interleukin, a growth factor, a polypeptide vaccine, an enzyme, an endorphin, a glycoprotein, a lipoprotein kinas, intra-cellular receptors, transcription factors, gene transcription activators/repressors, neurotransmitters (natural or synthetic), proteoglycans., a polypeptide involved in the blood coagulation cascade, that exerts its pharmacological effect systemically or any other polypeptide that has a molecular weight (Daltons) of up to 50 kDa or from the group consisting of proteins, polysaccharides, lipids, nucleic acids and combinations thereof or from the group consisting of leuprolide and albuterol or is among opiates or nicotine and nicotine derivates or scopolamin, morphine, apomorphine analoges or equivalent active substances or pharmaceutical active chemicals for asthma treatment, e.g. budesonid, salbutamol, terbutalinsulphate, salmeterol, flutikason, formoterol or salts thereof.

Figure 2:
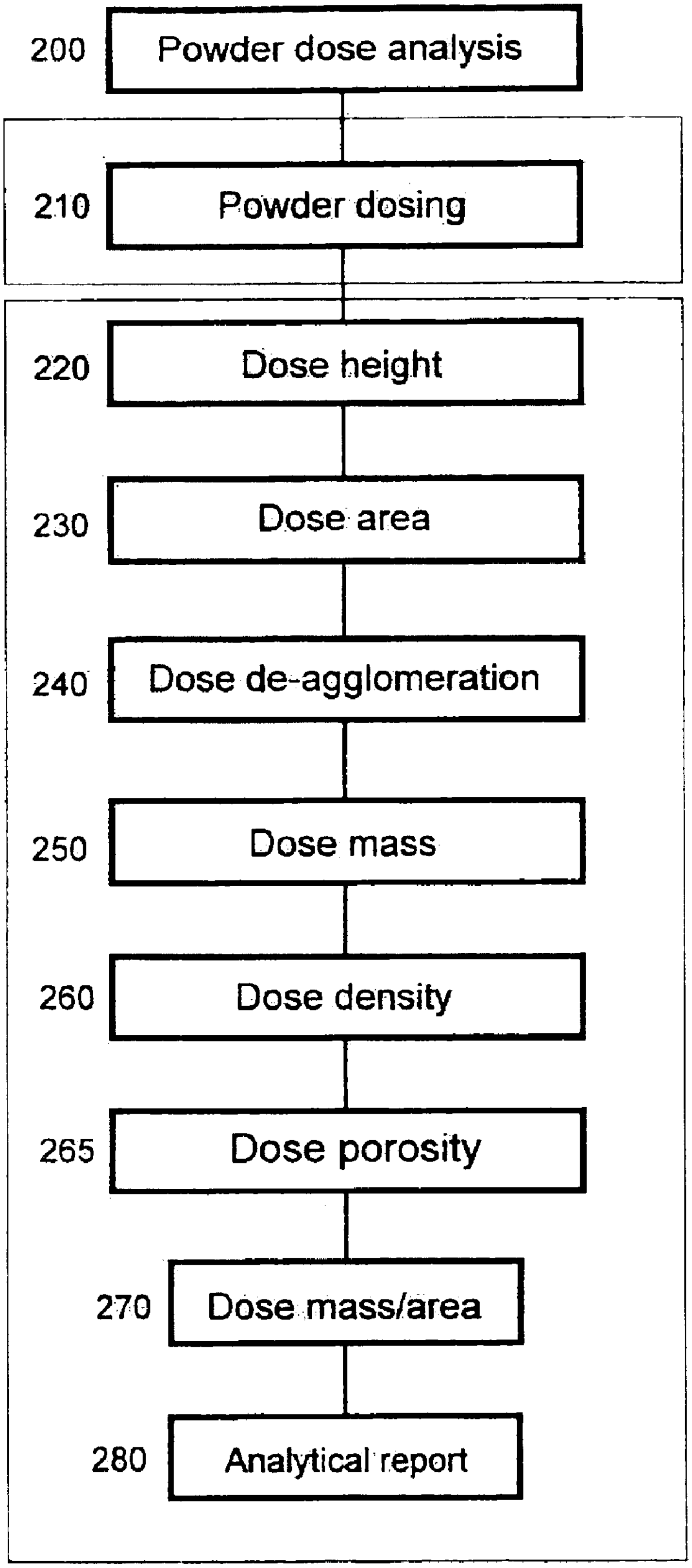
FIG. 2 is a flow chart illustrating the powder dose analysis when preparing the electro-dose.

The first step 110 of the powder dose analysis includes a series of at least five powder doses to be analyzed in a step 210 illustrated in FIG. 2. Standard settings of the input parameters are then used, which are well spread over an interval to have a possibility to in a sequence of steps 220 to 270 determine the most important specifications regarding height, area, mass, porosity and dose de-agglomeration at flow rate Q according to USP and $Q_{1\ kPa}$. Very important is to determine if a porosity adjustment is necessary to be performed by active use of mechanical and/or electrical methods in the preparation of the electro-powder into an electro-dose by adjusting the dose porosity to an optimum giving an optimum inhalation performance regarding de-agglomeration. The porosity of the electro-dose is then defined as $D_p=100-100\times(\text{density}_{electro\text{-}dose}/\text{density}_{electro\text{-}powder})$ producing a measure in percent.

Dose height is then measured in step 220 for the powder doses of step 210 using for instance a Laser displacement sensor from Keyence LK-031 with electronics LK-2001 and cables LK-C2 giving the height of the powder bed in μm.

The electro-powder doses tested in step 210 are then brought to step 230 for dose area investigation, wherein the projected size of the powder dose onto the device member is measured with, e.g., a stereo microscope from Olympus and noted down in millimeters with a resolution of 100 μm.

Figure 8:
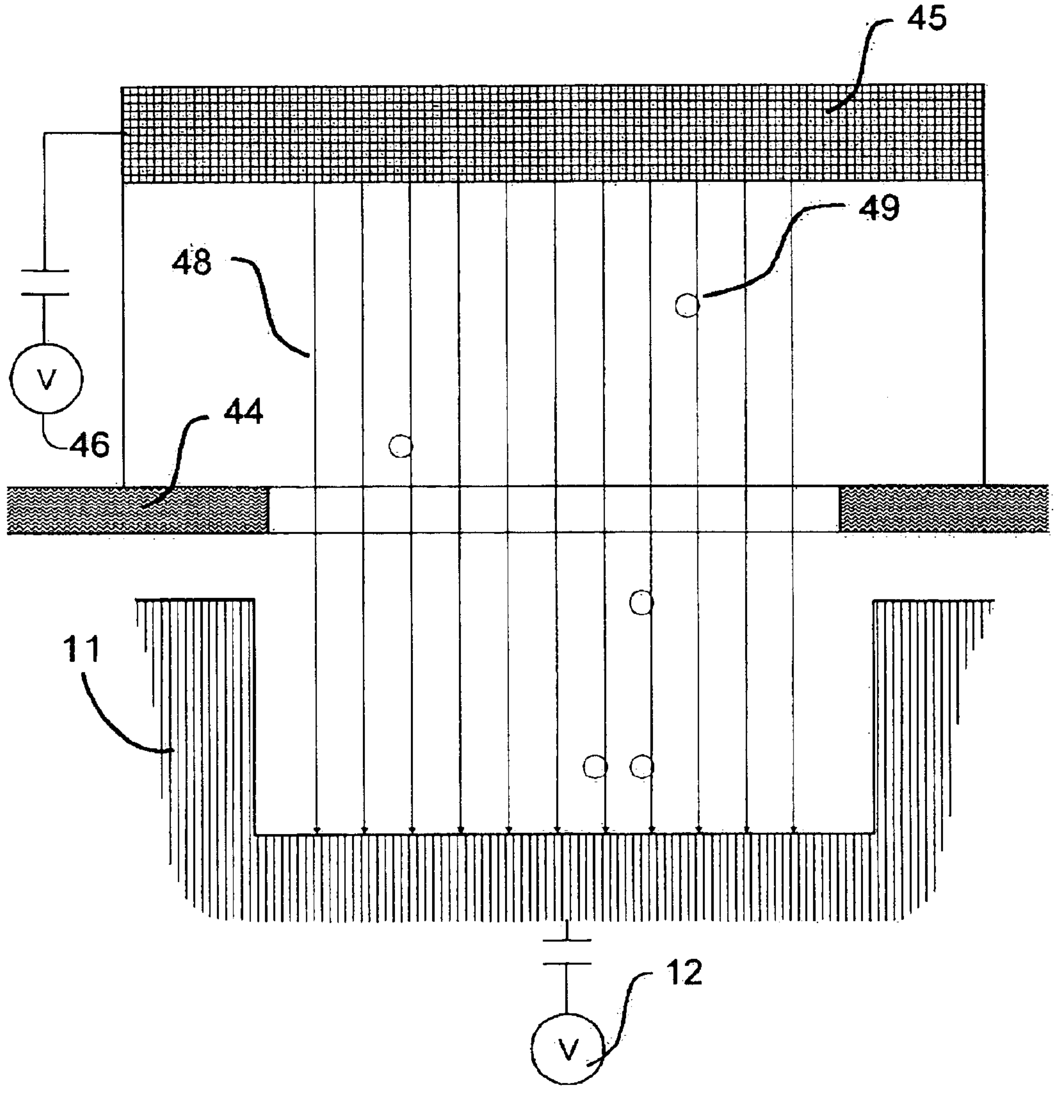
FIG. 8 illustrates transfer of electro-powder to a carrier by means of an electrostatic field.

A machine script is a program to control a sequence of operations inside a feeding device 45 in FIG. 8, which is a device that in a controlled way is feed ing electrostatically charged electro-powder into an electrical field allowing selected electro-powder particles with the right particle size to be transported to the device member and having a set of parameters added to the script to control the flexible settings of a powder dose. This electrostatic dosing device 45 is also performing a control of the absolute specific charge and all other essential parameters, e.g. feeding rate of de-agglomerated electro-powder by the machine script. The dose de-agglomeration step 240 is defined as breaking up agglomerated electro-powder by introducing electrical, mechanical, or aerodynamic energy. Usually de-agglomeration is performed as a stage one during dosing of the electro-powder and as a final stage two during the patient's inspiration of the electro-dose through the DPI. De-agglomeration is measured, e.g. using a Malvern Mastersizer as an example of a laser diffraction instrument used to measure particle size distribution both in aerosols and in liquids for physical size classification or an Andersen Impactor for an aerodynamic size classification as described in USP.

TABLE I

| Dosing Time (s) | Vibration KHz; μm | Frequency $t_1$; $t_2$; $E_1$; $E_2$ s; V | Electrical field E V/mm | Filter Potential $V_f$ | Machine Script |
|---|---|---|---|---|---|
| 8 | 0; 0 | 0.5; 0.01; 250; −50 | 250 | 600 | Test QC 1 |
| 8 | 0; 0 | 0.5; 0.01; 250; −50 | 250 | 600 | Test QC 1 |
| 8 | 0; 0 | 0.5; 0.01; 250; −50 | 250 | 600 | Test QC 1 |
| 8 | 0; 0 | 0.5; 0.01; 250; −50 | 250 | 600 | Test QC 1 |
| 8 | 0; 0 | 0.5; 0.01; 250; −50 | 250 | 600 | Test QC 1 |
| 8 | 0; 0 | 0.5; 0.01; 300; −50 | 300 | 650 | Test QC 1 |
| 8 | 0; 0 | 0.5; 0.01; 350; −50 | 350 | 700 | Test QC 1 |
| 8 | 0; 0 | 0.5; 0.01; 400; −50 | 400 | 750 | Test QC 1 |
| 8 | 0; 0 | 0.5; 0.01; 500; −50 | 500 | 800 | Test QC 1 |
| 8 | 0; 0 | 0.5; 0.01; 1000; −50 | 1000 | 1000 | Test QC 1 |

The electro-powder de-agglomeration is performed in the electrostatic feeding device 45 where de-agglomeration and classifying of the electro-powder is performed then resulting in obtaining a majority of the powder particles being in the correct size range 0.5–5 μm for being dosed onto the device member. This de-agglomeration is referred to as de-agglomeration #1 or electro-powder de-agglomeration.

The electro-dose de-agglomeration or de-agglomeration #2 takes place when sucking off the electro-dose from the device member accompanied with a de-agglomeration of the dose in the mouthpiece.

De-agglomeration #2 is measured as two different airflow values, whereby the first airflow Q is according to USP and the second airflow $Q_{1\ kPa}$ is at a pressure drop over the inhaler device of 1 kPa. The two different airflow values are for determining if an increase in inhalation energy has a major effect on the de-agglomeration #2. It is important to minimize the effect of the inhalation energy by adjusting the de-agglomeration #2 and the dosing properties and de-agglomeration # 1 to meet the electro-dose specification.

The electro-dose de-agglomeration is measured using a mouthpiece with a nozzle in the procedure which is identical to the construction and settings inside the DPI intended to be used and with a same device member as is to be used with the DPI. The portion at the end of the mouthpiece towards the a device member has to be aerodynamically correctly constructed to minimize retention.

Figure 17:
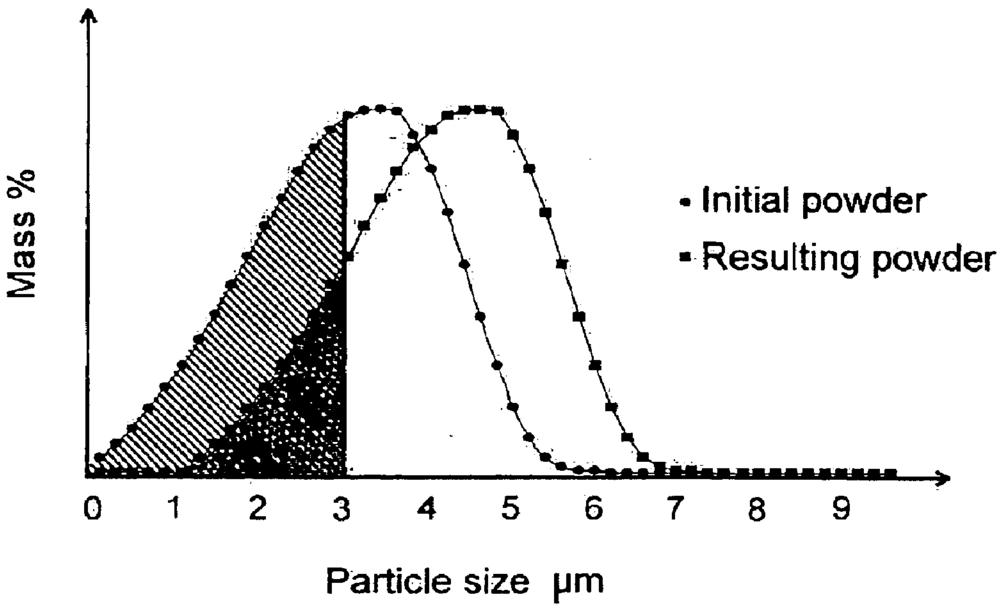
FIG. 17 is a graph representing calculation of de-agglomeration for particles up to 3 micrometers from an initial electro-powder particle size.
Figure 18:
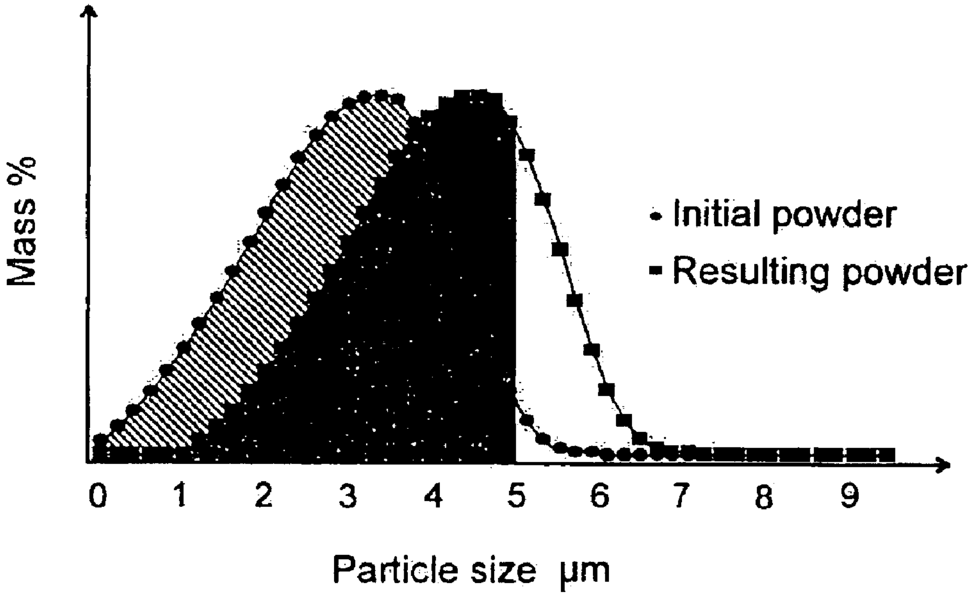
FIG. 18 is a graph representing calculation of de-agglomeration for particles up to 5 micrometers from an initial electro-powder particle size.

The de-agglomeration is then calculated using the electro-powder particle size specification as input material and the High Pressure Liquid Chromatography HPLC analysis regarding particle size distribution after a standard sucking off from the device member as the output result. The de-agglomeration of the electro-dose is then calculated as percent of de-agglomerated electro-dose at 3 µm, $DD_{3\ \mu m}$ and 5 µm, $DD_{5\ \mu m}$, compared to the amount of powder less than 3 µm and 5 µm in the original electro-powder. The de-agglomeration must be more than 25% to meet the electro-dose specification. FIG. 17 and FIG. 18 present calculations of de-agglomeration at 3 µm and 5 µm, respectively, in a graphical representation marking the areas under the particle size distribution curves for the initial and resulting distributions respectively. The curves plotted with dots representing initial electro-powder size distribution and the curves plotted with squares representing resulting electro-dose size distribution.

The dose mass in step 250 is possible to be measured in two different ways. First option is to use a Malvern Mastersizer, where the powder is collected on a filter after analysis through the instrument. The filter is then possible to analyze either using a balance, e.g. a Mettler Toledo UMT5 Ultra Microbalance or by chemical analyzes, e.g. a HPLC SpectraSYSTEM with a UV 6000 detector or any other suitable detector. A second option and also most preferable is to determine the powder mass using an Andersen Impactor and analyze both the aerodynamic particle size distribution and the total mass using for instance the HPLC Spectra-SYSTEM with a UV 6000 detector in accordance with USP.

To meet the electro-dose specification the mass must conform to the uniformity of dose stipulated in the USP and more preferable be between 95%<label claim<105% when this will be possible by a proper control regarding the electro-powder and the electrostatic dosing device together with the machine script.

Results from the above analysis: dose height in step 220, dose area in step 230, dose de-agglomeration in step 240 and dose mass in step 250 is noted down for calculations.

Dose density is calculated from dose mass in micrograms from step 250 divided by dose height in millimeters from step 220 and divided by dose area in $mm^2$ from step 230 and noted down as dose density in $\mu g/mm^3$ in step 260 Dose porosity in step 265 is here defined in percent as $D_p = 100 - 100 \times (\text{density}_{electro\text{-}dose}/\text{density}_{electro\text{-}powder})$ with the electro-powder density in this example being 1.4 $kg/dm^3$. Dose mass per dose area is calculated in step 270 as dose mass in µg from step 250 divided by dose area from step 230 and noted as $\mu g/mm^2$. The results are then combined with the settings presented in Table I and are presented with the results in Table II below.

Thus, all analytical results are noted down together with input data in an analytical report as step 280 forming a decision material for the step 120 of FIG. 1 determining dosing parameters. The result of calculated example illustrates that, in order to obtain a high quality dose with respect to de-agglomeration in step 240, the dose porosity obtained at step 265 should be to approximately 98%.

TABLE II

| Test | Dose height 220 µm | Dose area 230 $mm^2$ | Dose de-aggl. 240 3 µm % | 5 µm % | Dose mass 250 µg | Dose density 260 $\mu g/mm^3$ | Dose Po-rosity 265 % | Dose mass/area 270 $\mu g/mm^2$ |
|---|---|---|---|---|---|---|---|---|
| 1 | 196 | 40 | 80 | 82 | 77 | 9 | 99.4 | 1.9 |
| 2 | 92 | 40 | 81 | 84 | 73 | 20 | 98.6 | 1.8 |
| 3 | 76 | 40 | 81 | 85 | 75 | 25 | 98.2 | 1.9 |
| 4 | 64 | 40 | 84 | 87 | 78 | 30 | 97.9 | 2.0 |
| 5 | 69 | 40 | 83 | 89 | 77 | 28 | 98.0 | 1.9 |
| 6 | 124 | 40 | 77 | 84 | 173 | 35 | 97.5 | 4.3 |
| 7 | 137 | 40 | 74 | 81 | 214 | 39 | 97.2 | 5.4 |
| 8 | 148 | 40 | 66 | 73 | 365 | 62 | 95.6 | 9.1 |
| 9 | 135 | 40 | 63 | 68 | 415 | 77 | 94.5 | 10.4 |
| 10 | 124 | 40 | 58 | 64 | 520 | 105 | 92.5 | 13.0 |

The decision in step 120 determining dosing parameters is then used to make several powder dosing in a step 130 for tests and to verify that the chosen settings are correct and verified in a step 140 according to a repeated step of powder dose analysis. If the result of this powder dose analysis proves to be according to set specification for an electro-dose the settings is noted down for the continued manufacturing process.

Figure 3:
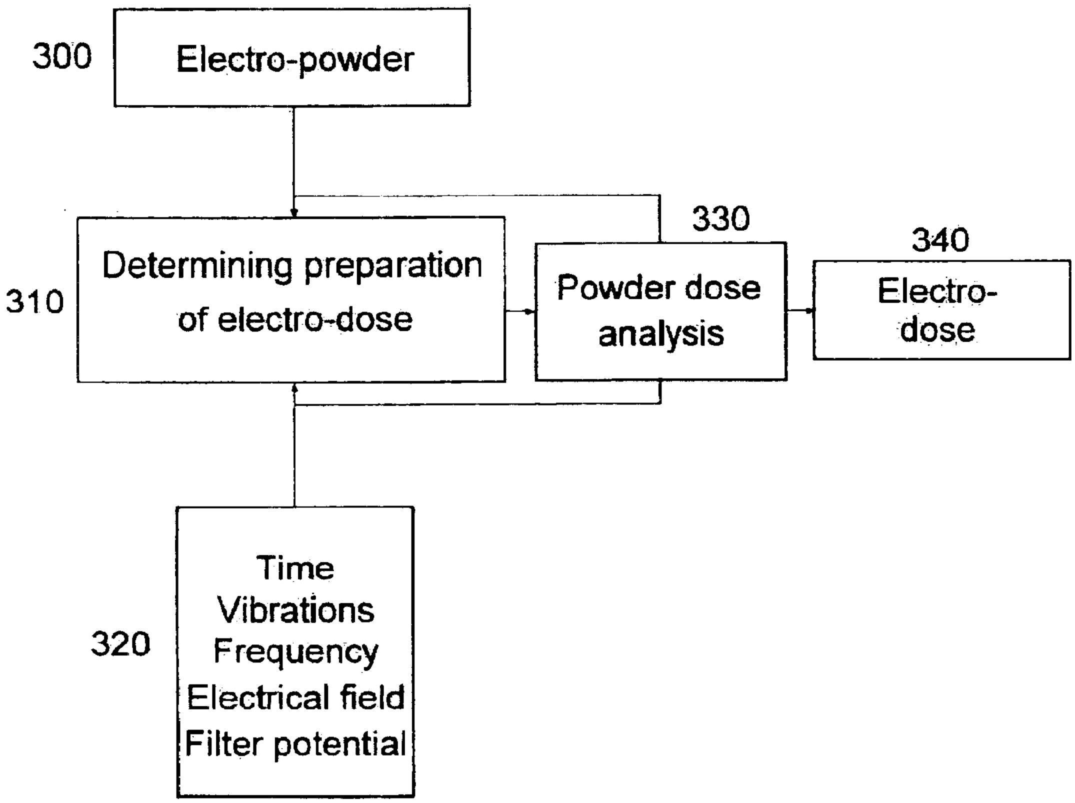
FIG. 3 is a summary flow chart illustrating preparation of the electro-dose.

On the other hand, if powder dosing according to step 130 results are not within set specification for an electro-dose, the result is in a step 145 returned to the step 120 of determining dosing and parameters for a new optimized parameter settings. The determining preparation of electro-dose as a step 310 in FIG. 3 is then taking into account the specification of the electro-powder in step 300 and dosing parameters in step 320 to have a new set of tests for the preparation of the electro-dose. A very useful tool to optimize the electro-dose is to use a statistical planning method for the tests to reduce the total amount of tests needed and fast finding the optimum preparation scheme for a desired electro-dose.

Figure 4:
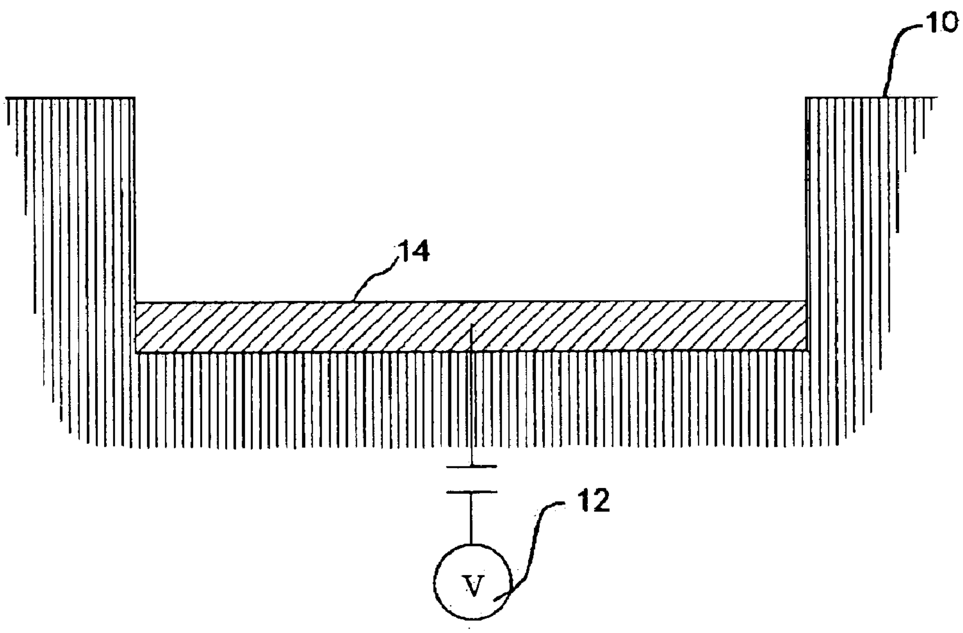
FIG. 4 illustrates a cross section of a dose carrier provided with a conducting or dissipative sheet for the preparation of an electro-dose by electrostatic methods.

FIG. 4 shows an illustrative cross section a device member with a dissipative or conductive carrier area 14 as a dose receiver for the electro-dose and an isolative material 10, e.g. plastic, having a surface resistance greater than $10^{11}$ ohms.

Figure 5:
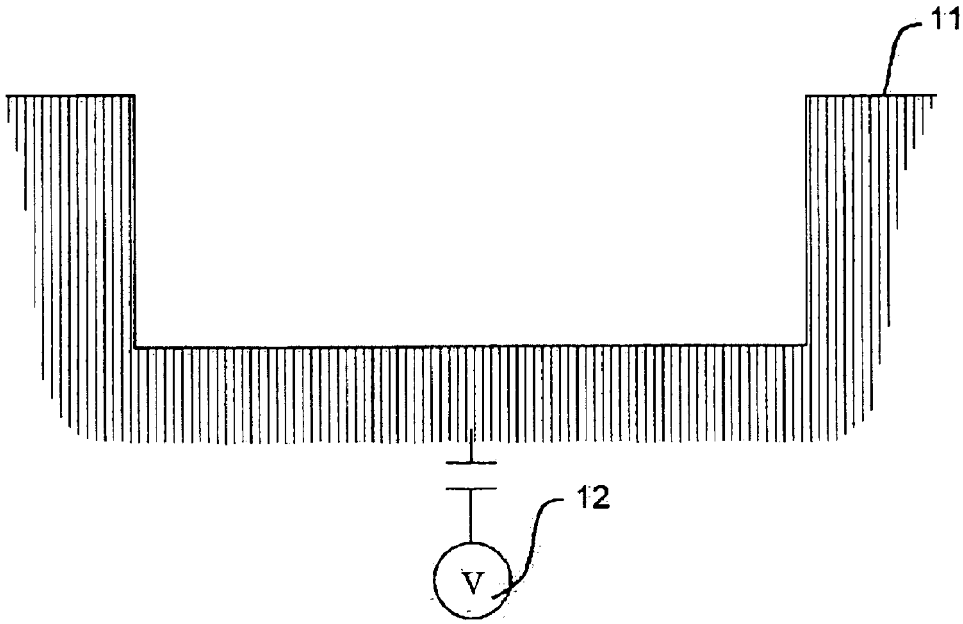
FIG. 5 illustrates a cross section of a dose carrier made from a conductive or dissipative material for the preparation of an electro-dose by electrostatic methods.

FIG. 5 illustrates a cross section with another material as walls where the dissipative or conductive material 11 has a potential defined through an applied voltage 12 and where a conductive material is a material with a surface resistance$<10^6$ ohms or a dissipative material with a surface resistance between the conductive and the isolative material $10^6$<Dissipative material<$10^{11}$ ohms.

Figure 6:
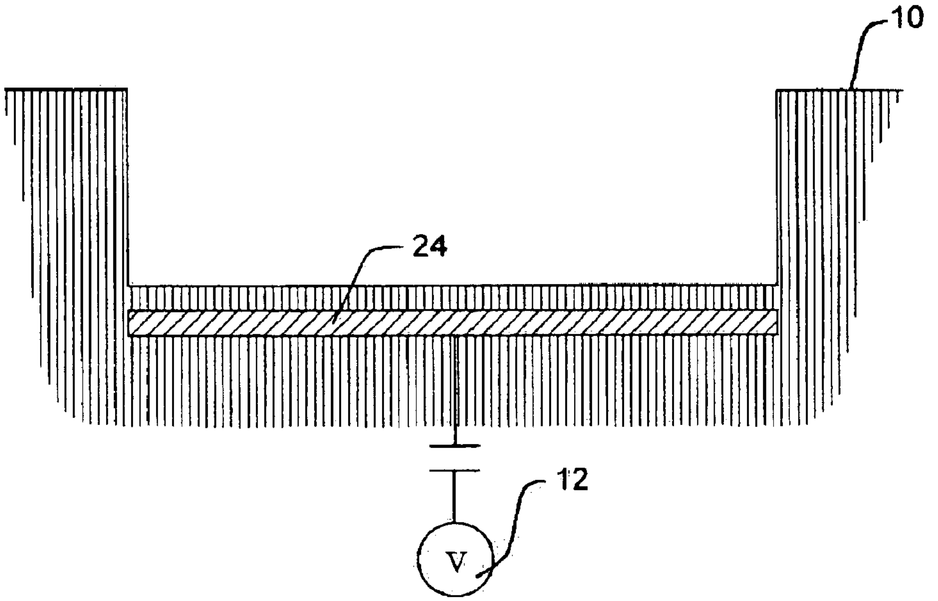
FIG. 6 illustrates a cross section of a dose carrier containing a buried conductive material sheet inside an isolative material for the preparation of an electro-dose by means of electrostatic methods.

FIG. 6 shows in an illustrative cross section a device member with a dissipative or conductive material area 24 located under or behind a thin layer approximately 10–3000 µm of isolative material 10 and where the dissipative or conductive material is having a set potential through an applied voltage 12.

Figure 7:
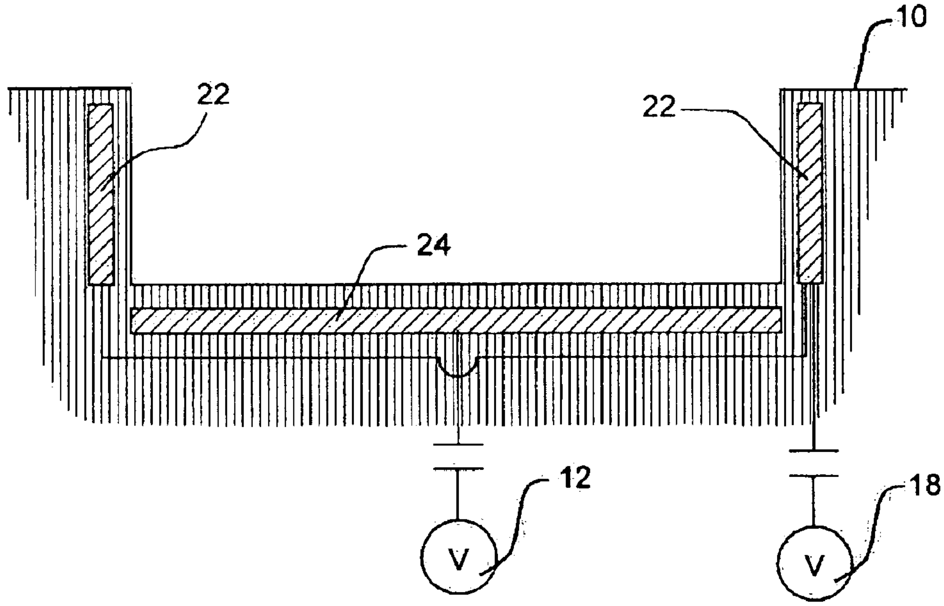
FIG. 7 illustrates a cross section of a dose carrier containing several separate buried conductive material sheets for the preparation of an electro-dose by electrostatic methods.

FIG. 7 shows an illustrative cross section of a device member with two separate dissipative or conductive materials 22 and 24 and a isolative material 10, where the dissipative or conductive material 24 forms the dose receiver of the electro-dose through a applied voltage 12 attracting the electrostatically charged electro-powder and the conductive material 22 is a conductive or dissipative material for applying a second electrical field to guide the powder to the correct position through a second applied voltage 18.

In a further illustrative embodiment similar to FIG. 5 the device member material forming the dose carrier may be chosen from an isolative plastic material, which is processed before dosing by ionized air to remove electrostatic charges from its surface. In another embodiment an isolative plastic material is processed before dosing by introducing the device member into humid air to remove electrostatic charge from its surface. In a third embodiment the device member isolative plastic material is processed before dosing by combination of ionized air and humid air to remove electrostatic charges from its surface.

In still a further embodiment the device member is temporarily given a dissipative surface by applying a thin solvent layer onto its surface, e.g. water, carbon dioxide or other non-toxic and FDA approved solvent. Such a solvent layer is then applied with appropriate electrical properties by using a temperature difference or a high humidity chamber and after dosing removing the solvent from the device member.

FIG. 8 shows in an illustrative example a dosing and metering set-up where a feeding device 45 for electrostatically charged electro-powder is subject to an electrical field 48 created by a separate applied potential 46 measured in V/mm and intended for transporting the electrostatically charged powder in a controlled way for dosing, metering or measuring purposes. A total field acts between the device member and the electro-powder feeder 45 through two different adjusted potentials 12 and 46. Between the feeder 45 and the device member is situated a filter 44 to shield part of the device member not to be subject to dosing until the device member is in the correct position and then having a transportation of electrostatically charged electro-powder particles 49 metered onto the carrier portion of the device member.

Figure 9:
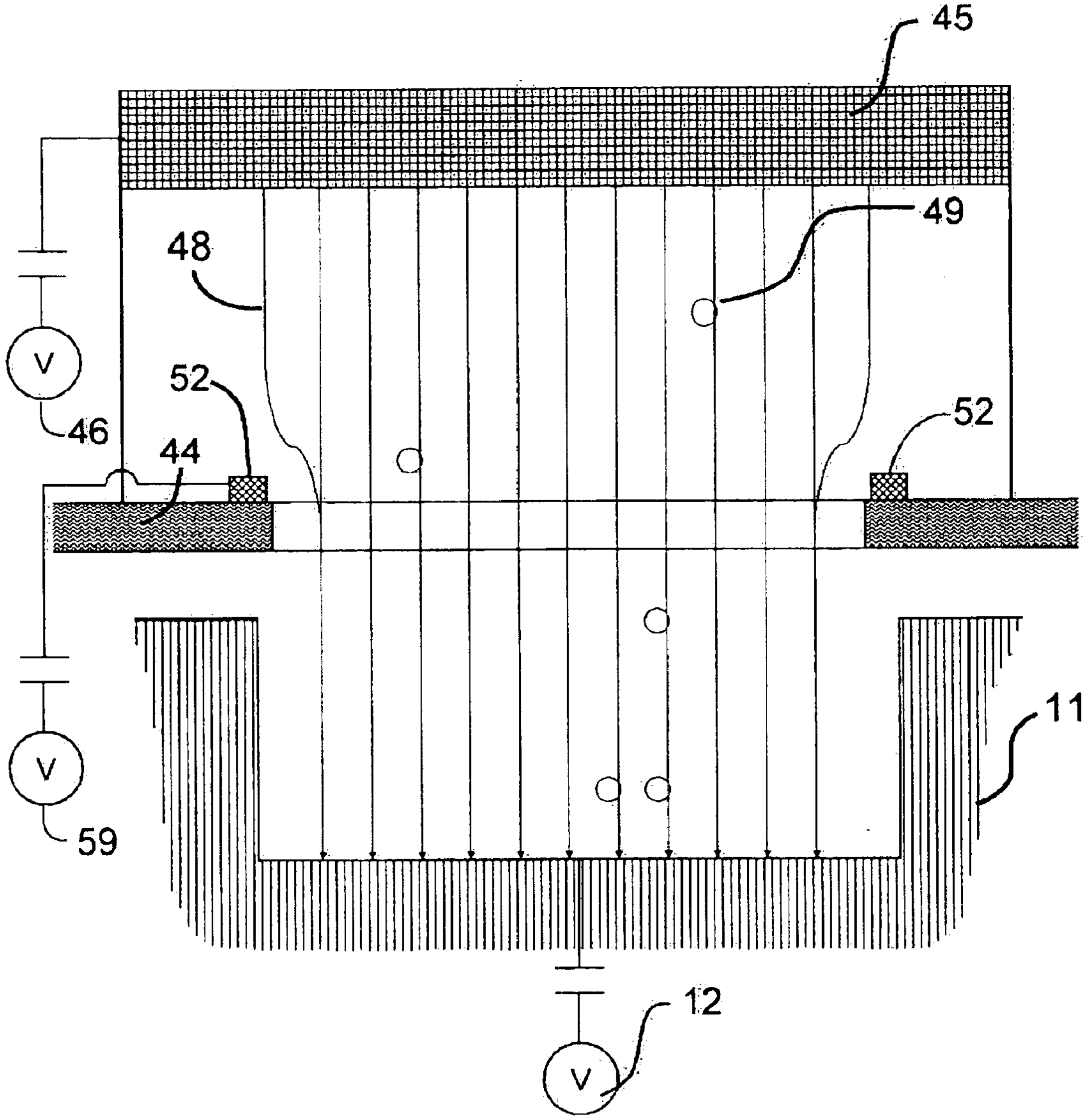
FIG. 9 illustrates transfer of electro-powder to the carrier by means of an electrostatic field and a focussing means.

FIG. 9 shows an illustrative example a dosing and metering set-up with a device member 11 made from a dissipative material at which powder is dosed by an applied electrical field between the feeder of electrostatically charged electro-powder 45 and the device member utilizing an electrical filter 52 with a applied make-up potential to guide the powder to the correct position onto the carrier portion of the device member. The filter potential also serves as a possibility to control depositing on and off in a simple way by switching the applied voltage to the filter between normal potential and a much lower potential compared to the potential applied to the device member in this example. The guiding of electrostatically charged electro-powder particles 49 is then a function of applied voltage of the feeder of electrostatically charged electro-powder 49 and the voltage applied to the device member 12 and the potential of the filter 52. The filter 52 is supported by an isolative filter holding material 44.

Figure 10:
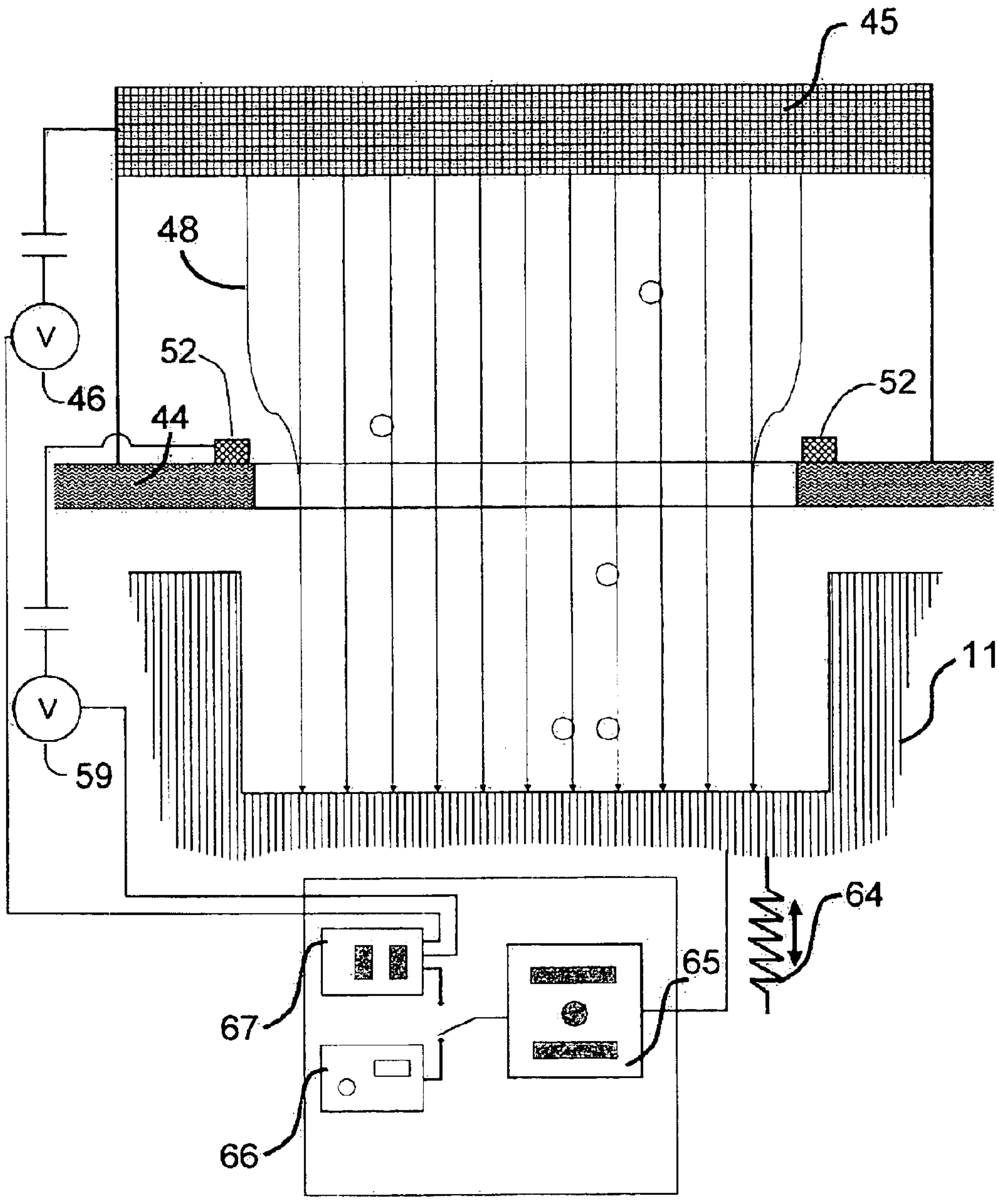
FIG. 10 illustrates a control circuitry utilized in the transfer of powder according to FIG. 9.

FIG. 10 shows in an illustrative example a dosing and metering set-up with a device member 11 in a dissipative material dosed onto by an applied electrical field between the feeder 45 of electrostatically charged electro-powder and the device member utilizing an electrical filter 52 with an applied make-up potential 59 to guide the powder to the correct position at the carrier portion of the device member 11. The filter potential also serves as a possibility to control deposition on and off in a simple way by changing the potential of the filter 52. The guiding of electrostatically charged electro-powder particles 49 is then a function of applied voltage to the feeder 45 of electrostatically charged electro-powder and the applied voltage to the device member 11 and the potential of the filter 52. The filter 52 is supported by an isolative filter holding material 44. The dose is possible to measure during the dosing and metering operation by using the electrometer 66 and switching the voltage 65 in front of a high voltage generator 67. During the dosing and metering operation it is also possible to control the density of the electro-dose by utilizing a mechanical vibration 64 or an electrical frequency utilizing, e.g. the switching box 65 resulting in a possibility to control the electrical field and the mechanical movement according to FIGS. 11 and 12.

Figure 11:
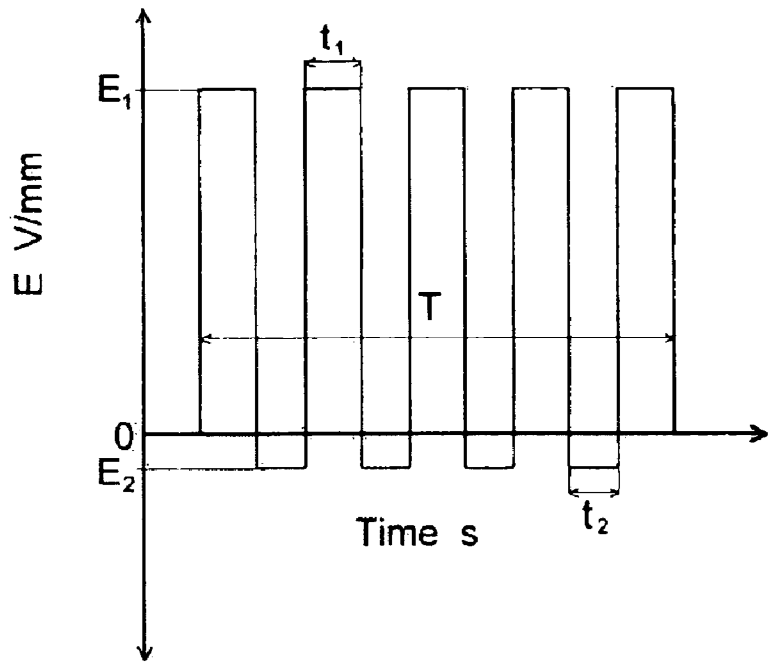
FIG. 11 illustrates an applied alternating electric field as function of time in transferring powder particles to the carrier.
Figure 16:
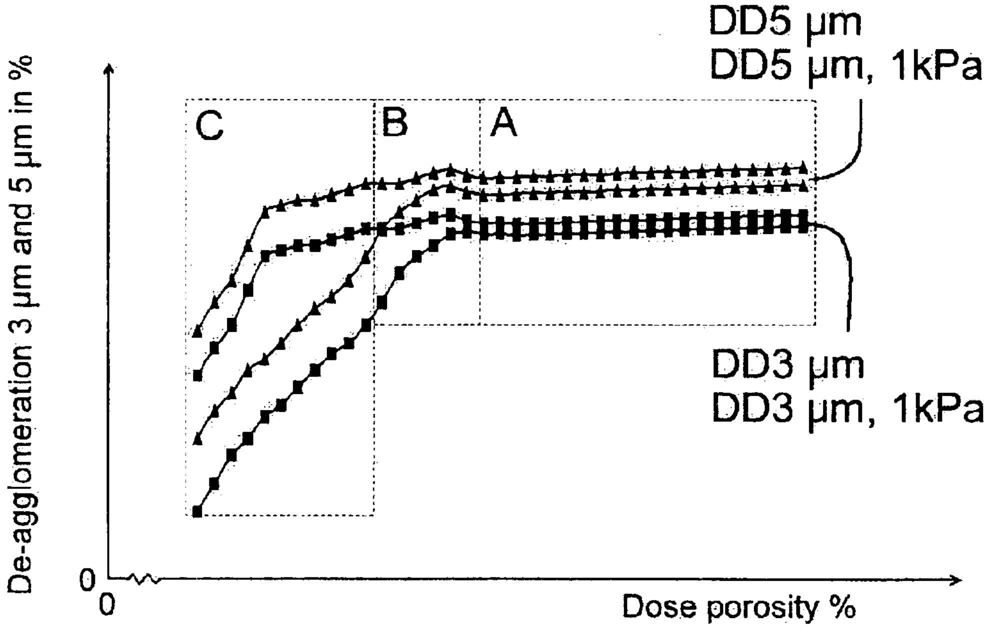
FIG. 16 is graph representing dose porosity and de-agglomeration for particles of sizes 3 and 5 micrometers.

FIG. 11 shows an example of electrical fields $E_1$ and $E_2$ applied as alternating fields at a pre-selected frequency to have the electro-powder to "dance" at the device member 11 to thereby achieve an optimum porosity for an optimum of de-agglomeration according to FIG. 16. FIG. 11 shows how the total dosing time period T is divided up in periods $t_1$ when the electrical field is at a maximum value of $E_1$ and other time periods $t_2$ when the electrical field is at a minimum value of $E_2$, whereby the time periods $t_1$ and $t_2$ are in the range $10^{-6}<t_1$, and $t_2<2$ seconds respectively.

Figure 12:
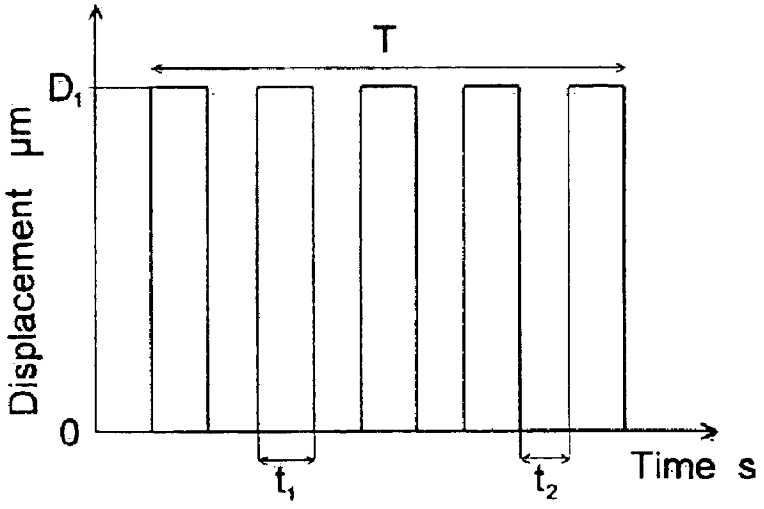
FIG. 12 illustrates displacement of carrier surface in micrometers as a function of time.

FIG. 12 illustrates an example of a set up with a mechanical vibration having a total dosing time period T and a maximum displacement of $D_1$ during $t_1$ and no displacement during the time period $t_2$ to make the dosed electro-powder particles to "dance" at the device member 11 and thereby, by means of a control of the applied field, having a controlled adjustment of the porosity to an optimum situation for an optimized de-agglomeration according to FIG. 16, whereby the time periods $t_1$ and $t_2$ are in the range $10^{-6}<t_1$and $t_2<2$ seconds, respectively.

Figure 13:
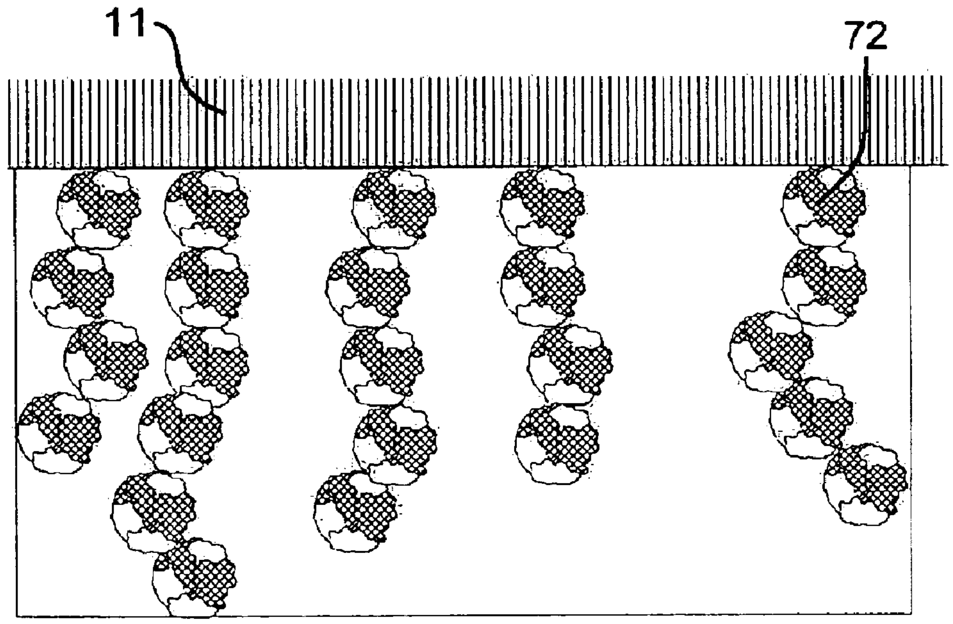
FIG. 13 illustrates a "tree" structure in an enlarged view initial positioning of de-agglomerated particles at the carrier surface.

FIG. 13 shows a "tree" structure of powder particles at the device member 11 showing the ordering of particles of an electro-dose not being subject to adjustment of dose porosity disclosing chains of powder rising from the device member. The electro-powder particles 72 are forming "trees" of particles resulting in an extremely high porosity. The porosity of an electro-dose is calculated using the width and height of the "tree" structure together with the length to calculate the volume and then dividing the mass of the electro-dose with the volume to obtain the density of the electro-dose. The porosity is then calculated as $D_p=100-100\times(\text{density}_{electro\text{-}dose}/\text{density}_{electro\text{-}powder})$ in percent, where the density of the electro-powder in this example is 1.4 $kg/dm^3$.

Figure 14:
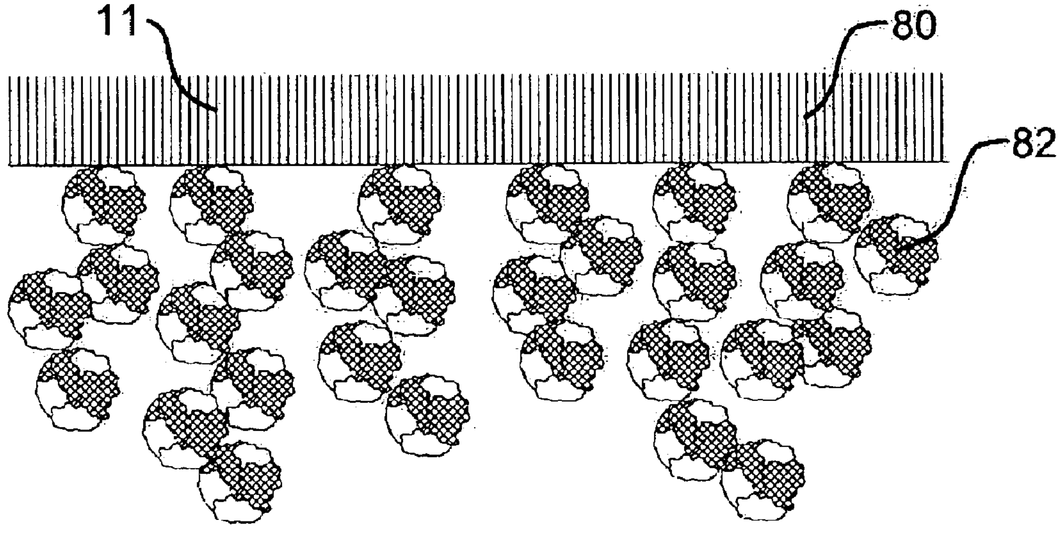
FIG. 14 illustrates a "sponge" structure in an enlarged view of particles positioned at the carrier surface after a compaction operation.
Figure 15:
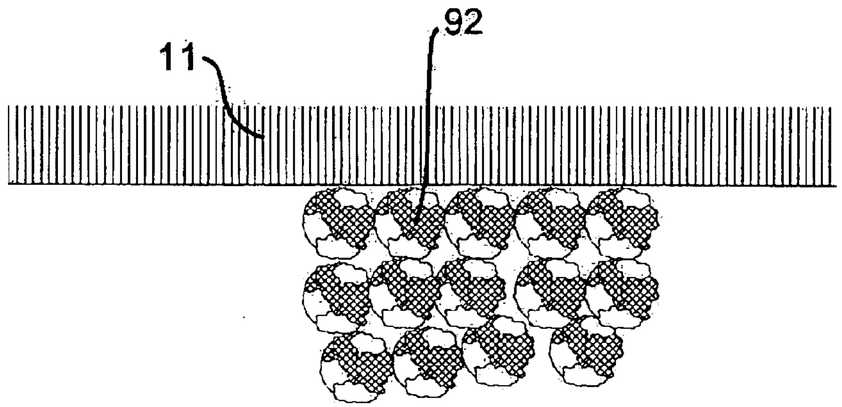
FIG. 15 illustrates in an enlarged view of a "velvet" structure of the particles at the carrier surface.

It should be noted that in the preferred process the carrier is turned with its receiving surface facing downwards as illustrated in FIGS. 13 to 15 when picking up the charged particles 72, 82 or 92. However, the process may also be performed as indicated by FIGS. 6 to 10.

FIG. 14 shows an electro-dose on the device member 11 with a "sponge" structure defined as an intermediate structure of the electro-dose, where some of the "tree" structures 82 have collapsed and are connected top to top forming a matrix with a medium to low density and less porosity through a adjusted density by electrical frequency or mechanical vibration during the dosing and metering operation thereby obtaining a lower porosity compared to the "tree" structure of FIG. 13.

FIG. 15 shows an electro-dose at a device member 11 presenting a velvet structure 92 after being porosity adjusted with the proper electrical frequency or mechanical vibration thereby obtaining a look like a smooth velvet cloth which shows much less porosity than the "sponge" structure.

FIG. 16 illustrates the effect of a dose porosity adjustment in which the de-agglomeration of the electro-dose is measured at different porosities showing an optimum de-agglomeration both for particles less than 5 $\mu$m and for particles less than 3 $\mu$m having a porosity in the range marked as A also indicating that the electro-dose is independent of the flow at porosities inside the range A.

In the range marked B the de-agglomeration is in a transition area and showing medium flow dependence and a lower grade of de-agglomeration. In range C the porosity is lower and the powder much harder to de-agglomerate in dose de-agglomeration and also showing a strong dependence of the flow i.e. the energy level of the de-agglomeration #2 and are not suitable as an dose for inhalation and subject to optimization. $DD_{5\ \mu m}$ is the dose de-agglomeration at 5 $\mu$m and at a differential pressure according to USP and $DD_{1\ kPa}$ is also according to USP but at a pressure drop over the inhaler of 1 kPa.

Figure 19:
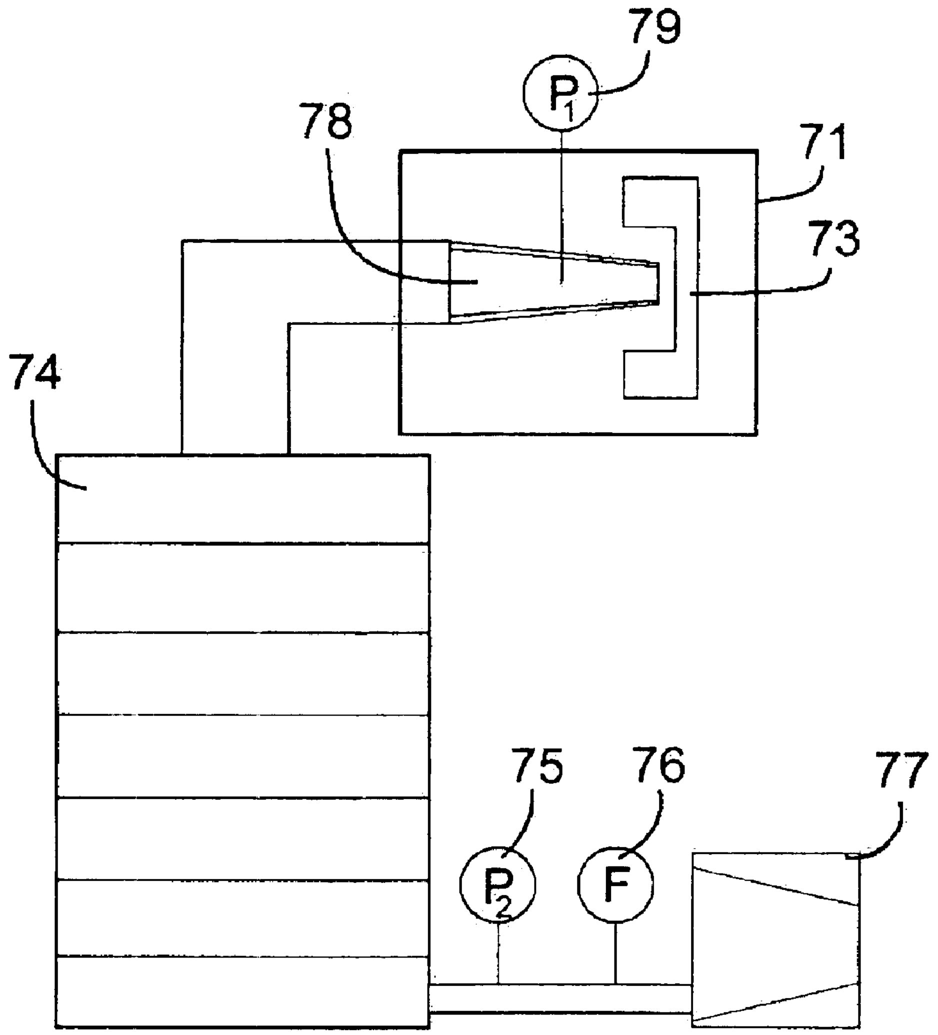
FIG. 19 shows a measurement set-up used for a measurement of size distribution and mass and further calculation of deagglomeration and flow rate.

Measurement of de-agglomeration is performed, e.g., according to FIG. 19, using an Andersen Inpactor together with a mouthpiece and a device member in a set-up identical with the intended DPI for the electro-dose or instead of the Andersen Impactor using a Malvern Master Sizer S to measure the physical particle size. When the particle distribution is measured the de-agglomeration can be calculated knowing the electro-powder particle size distribution.

The de-agglomeration is measured at two different rates of flow, flow-rate Q according to USP and at a flow-rate at 1 kPa pressure drop over the inhaler device according to USP. Measuring at two different flow-rates indicates if the electro-dose in the intended DPI is flow dependent or flow independent, as this may be an important aspect for the patient. If the difference in de-agglomeration is less than 25%, when calculated as (100−100×(de-agglomeration($Q_{1\ kPa}$)/de-agglomeration(Q)), then the electro-dose meets the specifications, if the result is outside the electro-dose specifications further optimization of the electro-dose has to be performed by going back to step 310.

FIG. 17 describes how the de-agglomeration at 3 $\mu$m is calculated using the initially input electro-powder under 3 $\mu$m represented by the hatched area as a base. The amount of de-agglomerated electro-powder from the electro-dose is then represented by the dark area under the curve showing resulting powder. By dividing the calculated value of the surface of the second area with the calculated value of the surface of the first area and multiplying by a factor 100 the de-agglomerated amount below 3 $\mu$m is obtained in percent.

FIG. 18 describes how the de-agglomeration at 5 $\mu$m is calculated using the initially input electro-powder under 5 $\mu$m represented by the hatched area as a base. The amount of de-agglomerated electro-powder from the electro-dose is then represented by the dark area under the curve showing resulting powder. By dividing the calculated value of the surface of the second area in FIG. 18 with the calculated value of the surface of the first area in FIG. 18 and multiplying by a factor 100 the de-agglomerated amount below 5 $\mu$m is obtained in percent.

FIG. 19 illustrates an example of a de-agglomeration and mass measurement set-up 71 identical to the inhaler to be used to determine the particle size distribution and mass from a pre-metered electro-dose sucked up from the device member 73 through a mouthpiece 78 using an Andersen Impactor 74 to determine the particle size distribution. The total pressure drop over the de-agglomeration set-up is measured with the pressure gauge 75 and the flow-rate of the air is measured with a flowmeter 76 in liters/minute. Suction may be achieved by means of a pumping device 77.

All measurements of the particle size distribution is measured at two different pressure drops over the inhaler device first all measurements are the performed according to USP and only the pressure is changed for the measurement at a lower pressure 1 kPa over the inhaler device 71 in point 79.

A complementary particle size distribution is also measured at 1 kPa pressure drop over the de-agglomeration #2 set-up 71 indicated by the pressure gauge 79 as differential pressure to the atmosphere and then the obtained flow rate is noted down and named $Q_{1\ kPa}$. The particle size distribution obtained at the flow rate $Q_{1\ kPa}$ is the compared with the particle size distribution obtained at the flow rate Q. the flow rate obtained by using all other settings according to the USP, and naming this flowrate $Q_{1\ kPa}$ and the resulting calculated. The result of the test of de-agglomeration #2 at two different pressures over the inhaler device and compared according to FIG. 16 to determine if the result meets the specification for an electro-dose and also if the de-agglomeration for 3 and 5 $\mu$m, $DD_{3\ \mu m,\ 1\ kPa}$ and $DD_{5\ \mu m,\ 1\ kPa}$ are within the specifications of the medical drug.

Thus the method and process according to the present disclosure will result in a very well defined electro-dose for utilization in a dry powder inhaler resulting in a small standard deviation of the doses for repeated administrations.

It will be understood by those skilled in the art that various modifications and changes may be made to the present invention without departure from the scope thereof, which id defined by the appended claims.

What is claimed is:

1. An electro-dose of a medical powder for use in a dry powder inhaler, the electro-dose having been prepared from an active powder substance or a dry powder medical formulation presenting a fine particle fraction (FPF) of the order 50% or more of its content having a particle size from 0.5 to 5 $\mu$m, said substance or formulation having been metered onto a device constituting a dose carrier, thereby having formed said electro-dose into a chosen state of dose porosity, the electro-dose further meeting electric specifications regarding absolute specific charge per mass after charging of the order 0.1 to 25 $\mu$C/g and presenting a charge decay rate constant $Q_{50}$ of more than 0.1 sec with a tap density of less than 0.8 g/ml and a water activity $a_w$ of less than 0.5.

2. The electro-dose according to claim 1, said metered electro-dose having, onto a surface area of said device member which forms a dose carrier, a height less than 800 $\mu$m.

3. The electro-dose according to claim 1, said metered electro-dose by using mechanical vibrations of the device member having been adjusted to a porosity having in percent a value between 75 and 99.9.

4. The electro-dose according to claim 1, said metered electro-dose, by using a frequency oscillation in an electrical field, having been adjusted to a porosity having in percent a value between 75 and 99.9.

* * * * *